United States Patent [19]

Richard et al.

[11] Patent Number: 5,714,134

[45] Date of Patent: Feb. 3, 1998

[54] PHOTOPROTECTIVE/COSMETIC COMPOSITIONS COMPRISING BENZOTRIAZOLE-SUBSTITUTED POLYORGANOSILOXANES/ POLYORGANOSILANES

[75] Inventors: Hervé Richard, Villepinte; Madeleine Leduc, Paris; Alain Lagrange, Couvray, all of France

[73] Assignee: Société L'Oréal S.A., Paris, France

[21] Appl. No.: 758,300

[22] Filed: Dec. 3, 1996

Related U.S. Application Data

[62] Division of Ser. No. 555,046, Nov. 8, 1995, Pat. No. 5,610,257.

[30] Foreign Application Priority Data

Nov. 8, 1994 [FR] France ................... 94 13395

[51] Int. Cl.$^6$ .................................................. A61K 7/42
[52] U.S. Cl. .................... 424/59; 424/70.9; 424/70.12; 424/70.122; 424/78.03
[58] Field of Search .......................... 424/78.03, 70.9, 424/70.12, 70.122, 59

[56] References Cited

U.S. PATENT DOCUMENTS

| | | | |
|---|---|---|---|
| 5,089,250 | 2/1992 | Forestier et al. | 424/70.9 |
| 5,164,462 | 11/1992 | Yang . | |
| 5,569,451 | 10/1996 | Richard et al. | 424/70.9 |
| 5,587,151 | 12/1996 | Richard et al. | 424/59 |

FOREIGN PATENT DOCUMENTS

| | | |
|---|---|---|
| 0388218 | 9/1990 | European Pat. Off. . |
| 0392883 | 10/1990 | European Pat. Off. . |
| 0478284 | 4/1992 | European Pat. Off. . |
| 92/19625 | 11/1992 | WIPO . |
| 93/04665 | 3/1993 | WIPO . |
| 93/10745 | 6/1993 | WIPO . |
| 94/06404 | 3/1994 | WIPO . |
| 94/10588 | 5/1994 | WIPO . |

*Primary Examiner*—Melvyn I. Marquis
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting effective amount of a novel benzotriazole-substituted polyorganosiloxane/polyorganosilane having one of the formulae (1) to (3):

$$B-\underset{R}{\overset{R}{Si}}-O-\left[\underset{R}{\overset{R}{Si}}-O\right]_r-\left[\underset{A}{\overset{R}{Si}}-O\right]_s-\underset{R}{\overset{R}{Si}}-B \quad (1)$$

$$\left[\underset{R}{\overset{R}{Si}}-O\right]_t\left[\underset{A}{\overset{R}{Si}}-O\right]_u \quad (2)$$

$$A-Si(R')_3 \quad (3)$$

wherein A is a monovalent benzotriazole radical which comprises an acrylate or acrylamide functional group, which is bonded directly to a silicon atom, and which has the formula (4):

$$\text{benzotriazole}-\text{OH}\begin{array}{l}-(X)_n\\-(Y)_m-\end{array} \quad (4)$$

$$-(CH_2-\underset{R^1}{\overset{}{CH}})_p-(CH_2)_q-Z-\underset{\overset{\|}{O}}{\overset{R^2}{C}}-CH-CH_2-$$

34 Claims, No Drawings

PHOTOPROTECTIVE/COSMETIC COMPOSITIONS COMPRISING BENZOTRIAZOLE-SUBSTITUTED POLYORGANOSILOXANES/ POLYORGANOSILANES

This application is a divisional of application Ser. No. 08/555,046, filed Nov. 8, 1995 U.S. Pat. No. 5,610,257.

CROSS-REFERENCE TO COMPANION APPLICATIONS

Our copending applications Ser. No. 08/555,334 filed Oct. 10, 1995, and Ser. No. 08/555,046 filed Nov. 8, 1995, both also assigned to the assignee hereof.

BACKGROUND OF THE INVENTION

1. Technical Field of the Invention

The present invention relates to novel compounds comprising short-chain, linear or cyclic diorganosiloxanes or triorganosilanes bearing at least one benzotriazole substituent which comprises an acrylate or acrylamide functional group.

This invention also relates to novel cosmetic compositions for topical application comprising said benzotriazole-substituted polyorganosiloxanes/polyorganosilanes, for the photoprotection of the skin and/or hair against ultraviolet radiation (such compositions hereinafter sometimes simply designated "sunscreen," "sunscreen/cosmetic" or "photoprotective/sunscreen" compositions).

2. Description of the Prior Art

It is known to this art that light radiation of wavelengths of from 280 nm to 400 nm promotes tanning of the human epidermis, and that irradiation of wavelengths of from 280 to 320 nm, i.e, UV-B irradiation, causes erythema and skin burns which can impair the development of a natural tan; hence, such UV-B radiation must thus be screened from the skin.

It is also known to this art that UV-A radiation, of wavelengths of from 320 to 400 nm, which tans the skin, also adversely affects it, in particular in the event of sensitive skin or skin constantly exposed to solar radiation. UV-A irradiation causes, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of compounds intended for the photoprotection (UV-A and/or UV-B) of human skin are known to this art.

Most of these are aromatic compounds displaying an absorption of UV radiation in the region from 280 to 315 nm or in the region of from 315 to 400 nm, or else in both of these regions together. They are, more often than not, formulated in sunscreen compositions as oil-in-water emulsions (namely, a cosmetically acceptable vehicle, carrier or diluent comprising an aqueous continuous dispersing phase and an oily discontinuous dispersed phase) which contain, at various concentrations, one or more traditional lipophilic and/or hydrophilic organic sunscreen compounds comprising an aromatic function suitable for selectively absorbing harmful or deleterious UV radiation. These sunscreen compounds (and the amounts thereof) are selected as a function of the desired specific sun protection factor (the specific protection factor (SPF) being expressed mathematically by the ratio of the irradiation time required to attain the erythemogenic threshold with the UV screening agent to the time required to attain the erythemogenic threshold in the absence of UV screening agent.)

Other than their sunscreen activity, these compounds having anti-UV properties must also display good cosmetic characteristics in the compositions comprised thereof, good solubility in common solvents, and especially fats such as oils and greases, and also good resistance to water and to perspiration (durability).

Among such prior art aromatic compounds, p-aminobenzoic acid derivatives, benzylidenecamphor derivatives, cinnamic acid derivatives and benzotriazole derivatives are particularly representative. However, certain of these compounds do not display all of the properties required for an acceptable UV screening agent in sunscreen compositions. In particular, their intrinsic screening activity may be insufficient, their solubility in the different formulations employed for photoprotection is not always sufficiently good (fat solubility in particular), they may not possess sufficient stability to light (photostability) and they may also display resistance to water and to sweat. It is also desirable that these sunscreen compositions do not penetrate the skin.

Thus, in the particular case of sunscreen compounds of the benzotriazole type, derivatives thereof have been prepared which have improved properties, especially in respect of their fat solubility and their cosmetic character, by effecting bonding of the benzotriazole screening group via grafting (hydrosilylation) onto a macromolecular chain of the silicone (organopolysiloxane) type. Such derivatives are described in EP-0,392,883, assigned to the assignee hereof, and are generally denominated "silicone screening agents", but the fat-solubility of these compounds can still be inadequate and, furthermore, in order to provide satisfactory sunscreen properties, it is often necessary to employ relatively large amounts of these photoprotective polymers, resulting in poor cosmetic properties in respect of the formulations comprised thereof.

SUMMARY OF THE INVENTION

Accordingly, a major object of the present invention is the provision of novel benzotriazole-substituted silicone/silane sunscreen compounds which display improved properties, in particular in respect of their solubility in fats, as well as regards their cosmetic properties.

Thus, it has now unexpectedly been determined that by bonding, in particular via hydrosilylation, one or more specific benzotriazole derivatives, namely, one or more benzotriazole compounds which comprise an acrylate or acrylamide functional group, to a particular linear or cyclic silicone chain or a particular silane, novel silicone/silane sunscreen compounds are prepared which avoid or conspicuously ameliorate the above disadvantages and drawbacks of the prior art silicone sunscreens, said novel compounds displaying, in particular, very high sunscreen activity, both in the UV-A range and in the UV-B range, very good solubility in the common organic solvents and notably in fatty substances such as oils, and also excellent cosmetic properties, rendering same particularly well suited for formulation into photoprotective/cosmetic compositions for protecting the skin and/or the hair against the damaging or deleterious effects of ultraviolet radiation.

Briefly, the present invention features novel compounds having one of the following formulae (1) to (3):

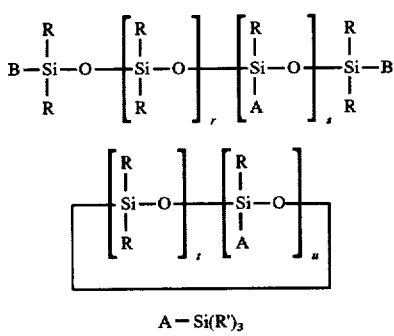

(1)

(2)

A—Si(R')₃     (3)

in which the radicals R, which may be identical or different, are each a $C_1$–$C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $C_1$–$C_8$ alkyl radical or a phenyl radical; r is an integer ranging from 0 to 50, inclusive, and s is an integer ranging from 0 to 20, inclusive, with the proviso that, if s is zero, then at least one of the two radicals B is a radical A; u is an integer ranging from 1 to 6, inclusive, and t is an integer ranging from 0 to 10, inclusive, with the proviso that t+u is equal to or greater than 3; and the radical A is a monovalent radical bonded directly to a silicon atom and which has the following formula (4):

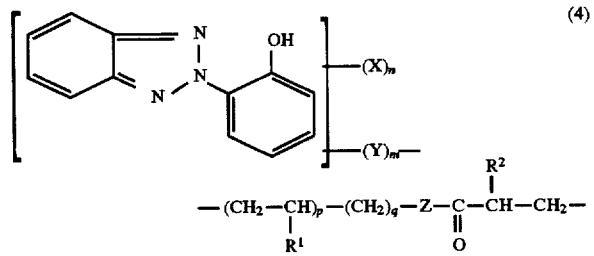

(4)

wherein n is an integer ranging from 0 to 3, inclusive, and the radicals X, which may be identical or different, are each a $C_1$–$C_8$ alkyl radical, a halogen atom or a $C_1$–$C_4$ alkoxy radical; m is 0 or 1, and Y is —O—, —NH—, —COO—, —O(CH₂)ᵥ—COO— or —(CH₂)ᵥ—OCONH— in which v and w are integers ranging from 0 to 12, inclusive; R is 0 or 1; g is an integer ranging from 0 to 12, inclusive; Z is —O— or —NH—; $R^1$ is hydrogen or a $C_1$–$C_4$ alkyl radical; and $R^2$ is hydrogen or a methyl radical.

DETAILED DESCRIPTION OF BEST MODE AND PREFERRED EMBODIMENTS OF THE INVENTION

More particularly according to the present invention, in the above formulae (1) to (3), A is thus the radical derived from the benzotriazole which, after bonding to the starting short silicone chain or to the starting silane, imparts absorbing properties to the compounds of linear diorganosiloxane type (formula (1)), or of cyclic diorganosiloxane type (formula (2)), or of triorganosiloxane type (formula (3)), both with respect to UV-A and UV-B radiation. As indicated above, and as is apparent from the definition of the above formula (4), this group necessarily comprises either one acrylate function (Z=O) or one acrylamide function (Z=NH) which is provided by the linking or bridging moiety which couples the benzotriazole to the silicone chain or to the silane.

Also as is apparent from the above formula (4), the coupling of the linking radical —(Y)ₘ—(CH₂—CHR¹)ₚ—(CH₂)ₐ—Z—CO—CHR²—CH₂— to the benzotriazole nucleus thus bonds the benzotriazole nucleus to a silicon atom of the silicone backbone or of the silane, and this substitution can be effected at all available positions afforded by the two aromatic rings of the benzotriazole:

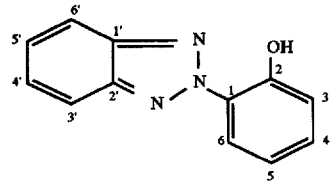

Preferably, this coupling is at positions 3, 4, 5 (aromatic ring bearing the hydroxyl function) or 4' (benzene ring fused to the triazolyl ring), and even more preferably at positions 3, 4 or 5.

Likewise, the coupling of the substituent X can be at all other available positions of the benzotriazole. However, this coupling is preferably at positions 3, 4, 4', 5 and/or 6.

In the above formulae (1) to (3), the alkyl radicals can be linear or branched and are advantageously selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R, R' and B according to the invention are methyl, ethyl, propyl, n-butyl, n-octyl and 2-ethylhexyl radicals. Even more preferably, the radicals R, R' and B are all methyl radicals.

Among the compounds of the above formulae (1) to (3), preferred are those corresponding to formula (1) or to formula (2), namely, linear or cyclic short-chain diorganosiloxanes.

Among the linear or cyclic diorganosiloxanes according to the present invention, preferred are the random derivatives or well-defined block derivatives having at least one, and more preferably all of the following definitions:

R is alkyl and, even more preferably, is methyl,

B is alkyl and, even more preferably, is methyl (in the case of the linear compounds of formula (1)), r ranges from 0 to 3, inclusive; s ranges from 0 to, 3 inclusive (in the case of the linear compounds of formula (1)), t+u ranges from 3 to 5 (in the case of the cyclic compounds of formula (2)), n is not zero and is preferably equal to 1 or 2, and X is then selected from among methyl, tert-butyl or $C_1$–$C_4$ alkoxy radicals, preferably a methoxy radical, m is not zero and Y is —O— or p is not zero and R q ranges from 0 to 3, inclusive, and Z is —O— or —NH—.

To prepare the silicone sunscreen agents of formulae (1) and (2), a first technique (Method 1), can be employed, namely, a traditional hydrosilylation reaction:

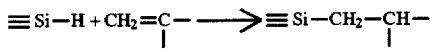

starting from the corresponding silicone in which, for example, all of the radicals A are hydrogen atoms. This starting silicone will hereinafter be designated derivative containing SiH; the SiH groups may be present in the silicone backbone and/or at the ends of the silicone chain. These derivatives containing SiH are well known compounds in the silicone industry and are generally commercially available. They are described, for example, in U.S. Pat. Nos. 3,220,972, 3,697,473 and 4,340,709.

This derivative containing SiH may thus be represented either by the following formula (1a):

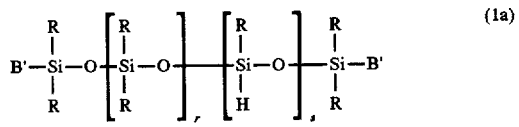
(1a)

in which R, X and s are as defined above in respect of the formula (1) and the radicals B', which may be identical or different, are selected from among the radicals R and a hydrogen atom, or by the following formula (2a):

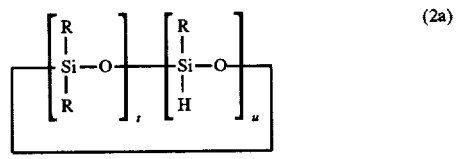
(2a)

in which R, t and u are as defined above in respect of the formula (2).

A conventional hydrosilylation reaction is thus carried out on this SiH-containing derivative of formula (1a) or (2a), conducted in the presence of a catalytically effective amount of a platinum catalyst, with an organic benzotriazole compound having the following formula (4a):

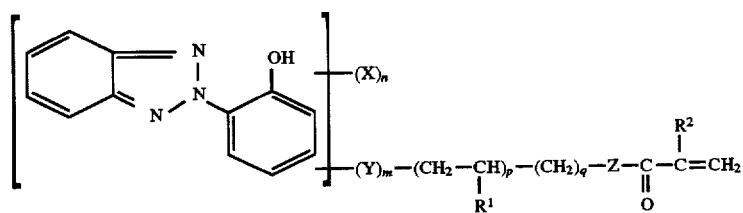
(4a)

in which X, Y, Z, R¹, R², n, m, p and q are as defined above in respect of the formula (4).

Processes suitable for the preparation of the above compounds of formula (4a) are described, in particular, in U.S. Pat. Nos. 4,316,033 and 4,328,346. Moreover, certain of these compounds are commercially available. In particular, 2-(2'-hydroxy-5-methacrylyloxyethylphenyl)-2H-benzotriazole is marketed under the trademark "Norbloc 7966®" by Noramco.

In addition, the working conditions to be observed for conducting the hydrosilylation reaction between the compounds of formula (1a) or (2a) above with the compound of formula (4a) above are reported in the aforesaid EP-0,392,883, hereby expressly incorporated by reference.

As regards the photoprotective agents of the triorganosilane type of formula (3), these can be prepared via hydrosilylation reaction between a starting silane of formula (R')₃Si—H (formula (3a)), in which R' is as defined above in respect of the compounds of formula (3), and an organic benzotriazole derivative of above formula (4a).

Exemplary compounds of formula according to the present invention include the following:

(a) 2-(2'-hydroxy-5'-methacrylyloxyethylphenyl)-2H-benzotriazole;

(b) 5-methoxy-2-(2'-hydroxy-4'-methacrylyloxyphenyl)-2H-benzotriazole;

(c) 5-methoxy-2-(2'-hydroxy-3'-tert-butyl-5'-methacrylyloxyethylphenyl)-2H- benzotriazole;

(d) 5-methyl-2-(2'-hydroxy-5'-methacrylyloxyethyloxyphenyl)-2H-benzotriazole;

(e) 5-methacrylyloxyethyl-2 -(2'-hydroxy-3',5'-di-tert-butylphenyl) -2H-benzotriazole.

Another synthesis (Method 2) which is suitable for the preparation of the silicone-containing sunsceen agents of formulae (1) and (2) employs starting compounds corresponding to formula (1) or (2) in which all of the radicals A are replaced by the radical of formula (5):

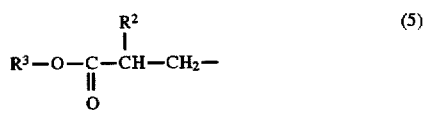
(5)

in which R² is as defined above and R³ is a hydrogen atom or a methyl or ethyl radical.

The alcohol, the phenol or the amine corresponding to formula (4b):

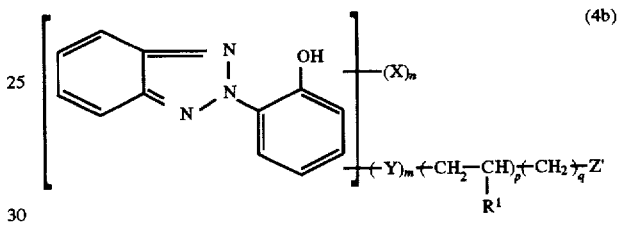
(4b)

in which X, Y, R¹, n, m, p and q are as defined above in respect of the formula (4) and Z' is —OH or —NH₂, is then reacted with this carboxylic siloxane derivative.

Relative to the silicone photoprotective agents of the prior art, such as those described in EP 0,392,883, the benzotriazole-substituted silicone/silane sunscreen agents according to the invention exhibit one or more essential structural differences which are the source of their exceptional properties: the silicone chains onto which the benzotriazole structural unit is grafter are, on the one hand, much shorter, and, on the other, the structural unit derived from the benzotriazole always comprises at least one acrylate or acrylamide functional group.

Also as indicated above, the compounds of formulae (1) to (3) above excellent intrinsic screening activity with respect to UV-A and UV-B ultraviolet radiation. In addition, taking account of their highly liposoluble nature, the compounds of formulae (1) to (3) may be used in high concentrations, thereby imparting very high specific protection factors to the final compositions; moreover, they distribute themselves uniformly in standard cosmetic vehicles comprising at least one fatty phase or at least one cosmetically acceptable organic solvent, and may thus be applied to the skin or hair to form an effective protective film. Too, their cosmetic properties are very good, namely, in particular, compared with the silicone screening agents of the prior art, these products are less sticky and render the skin or hair softer.

Thus, the present invention also features cosmetic compositions comprising, in a cosmetically acceptable vehicle, carrier or diluent, preferably including at least one fatty phase or at least one organic solvent, an effective photoprotective amount of at least one compound of the above formulae (1) to (3).

The compounds of formulae (1) to (3) are advantageously present in proportions ranging from 0.1% to 20% by weight, and preferably from 0.5% to 10% by weight, relative to the total weight of the composition.

The cosmetic compositions of the invention may be used as compositions for protecting the human epidermis or hair against ultraviolet rays, as sunscreen compositions or as makeup products.

These compositions may, in particular, be in the form of a lotion, a thickened lotion, a gel, a cream, an ointment, a milk, a powder or a solid stick and may optionally be packaged as an aerosol, as a foam, a mousse or a spray.

They can contain the usual cosmetic adjuvants and additives, such as fats and fatty substances, organic solvents, silicones, thickeners, softeners, emollients, complementary sunscreens, anti-foaming agents, moisturizing or hydrating agents, fragrances and perfumes, preservatives, surfactants, fillers, sequestering agents, anionic, cationic, nonionic or amphoteric polymers or mixtures thereof, propellants, basifying or acidifying agents, colorants, dyes, pigments or nanopigments, in particular those designed to provide a complementary photoprotective effect by physically blocking out ultraviolet radiation, or any other ingredient customarily used in cosmetics, especially for the production of sunscreen compositions.

Exemplary of the organic solvents are the lower alcohols and polyols, such as ethanol, isopropanol, propylene glycol, glycerol and sorbitol.

The fats or fatty substances can comprise of an oil or wax or mixtures thereof, fatty acids, fatty acid esters, fatty alcohols, petrolatum, paraffin, lanolin, hydrogenated lanolin or acetylated lanolin. The oils may be selected from among animal, vegetable, mineral or synthetic oils and, in particular, hydrogenated palm oil, hydrogenated castor oil, liquid petrolatum, liquid paraffin, puncellin oil, volatile or non-volatile silicone oils, and isoparaffins.

When the cosmetic composition according to the invention are used for protecting the human epidermis against the deleterious or damaging effects of UV irradiation or as sunscreen compositions, they are advantageously formulated as a suspension or dispersion in solvents or fatty substances, or, alternatively, in the form of an emulsion (in particular of O/W or W/O type, but preferably of O/W type) such as a cream or a milk, or of a vesicle dispersion, or as an ointment, a salve, a gel, a solid stick or an aerosol foam. The emulsions may additionally contain anionic, nonionic, cationic or amphoteric surface-active agents.

When the cosmetic compositions according to the invention are used for the photoprotection of the hair, they can be formulated as a shampoo, a lotion, a gel or rinse, to be applied before or after shampooing, before or after dyeing or bleaching, before, during or after permanent-waving or straightening of the hair, or as a styling or treatment lotion or gel, a blow-drying or hair-setting lotion or gel, a hair lacquer, a permanent-waving or hair-straightening composition, or a composition for dyeing or bleaching the hair.

When the cosmetic compositions according to the invention are used as makeup products for the eyelashes, the eyebrows, the skin or the hair, such as a skin-treatment cream, a foundation, a lipstick, an eye shadow, a blush, an eyeliner, a mascara or a coloring gel, they can be formulated in solid or pasty, anhydrous or aqueous form, such as oil-in-water or water-in-oil emulsions, suspensions or gels.

The cosmetic treatment of the skin or hair to protect same against the deleterious effects of ultraviolet radiation, in particular solar radiation, comprising topically applying to the skin or hair an effective amount of a sunscreen/cosmetic composition as described above, or of a compound of the above formulae (1) to (3).

In order to further illustrate the present invention and the advantages thereof, the following specific examples are given, it being understood that same are intended only as illustrative and in nowise limitative.

EXAMPLE 1

This example relates to the preparation (according to Method 1) of a compound in accordance with the present invention, having the structural formula:

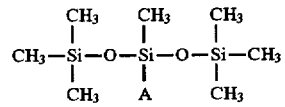

in which A is the radical:

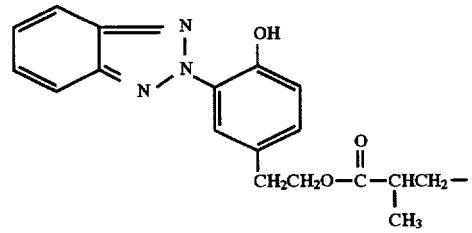

(this compound has formula (1) in which R=B=CH$_3$; r=0; s=1; n=0; m=0; q=2; R$^2$=CH$_3$).

30 g of 2-(2'-hydroxy-5-methacrylyloxyethylphenyl)-2H-benzotriazole ("Norbloc 7966®") and 50 ml of toluene were introduced into a reactor. The mixture was heated to 80° C., under nitrogen. The hydrosilylation catalyst (complex containing 3–3.5% of Pt in cyclovinylmethylsiloxane, marketed by Hüls under the trademark Petrarch PC085: 100 µl) was added, followed by 24.5 g of heptamethyltrisiloxane. After 67 hours at 80° C. under nitrogen, with 50 µl additions of catalyst every 12 hours, the reaction medium was concentrated and chromatography was then carried out on silica under pressure (eluent: heptane with a 0–50% gradient of CH$_2$Cl$_2$). 5.1 g of the desired final product, which was in the form of a pale yellow oil, were thus recovered.

The UV absorption characteristics (measured in ethanol) of this compound were as follows:

| | |
|---|---|
| λ$_{max}$:337 nm | ε$_{max}$: 17 500 |
| λ$_{max}$:298 nm | ε$_{max}$: 14 550 |

This compound is thus a very effective sunscreen which is active in the UV-A and UV-B range.

EXAMPLE 2

This example relates to the preparation, but in this instance via Method 2, of the same compound as prepared in Example 1.

(a) First stage 34.24 g of ethyl methacrylate containing a spatula-tipful of 4-hydroxyanisole were heated to 80° C., under nitrogen, in a reactor. The hydrosilylation catalyst (complex containing 3–3.5% of Pt in cyclovinylmethylsiloxane, marketed by Hüls under the trademark Petrarch PC085: 200 µl) was added thereto, followed by dropwise addition, over 30 minutes, of 73.42 g of heptamethyltrisiloxane. After stirring for 3 hours at 80° C. under nitrogen, the medium was concentrated, the acrylate and the siloxane in excess were evaporated off and a pale yellow oil was thus recovered. This oil was then distilled under vacuum. The fraction distilling at 48°–52° C. at 20 mmHg corresponded to the desired compound of formula (1) in which $R=B=CH_3$; $r=0$; $s=1$; and A was the radical of formula (5) wherein $R^2$=methyl and $R^3$=ethyl.

(b) Second stage 340 ml of toluene, 20 g of the compound prepared in Stage (a) and 12.7 g of 2-(2'-hydroxy-5'-hydroxyethylphenyl)-2H-benzotriazole (i.e., a compound of formula (4a) in which $n=0$; $m=0$; $p=1$; $R^1=H$; $q=0$ and $Z'=OE$) were introduced into a reactor fitted with Dean-Stark apparatus. 0.5 g of p-toluenesulfonic acid was added and the mixture was heated at reflux for 20 hours with removal of the ethanol formed. The reaction medium was concentrated and chromatography was then carried out on silica under pressure (eluent: heptane with a 0–50% gradient of $CH_2Cl_2$). 9.8 g of the desired final product, which corresponded to the compound prepared in Example 1, were thus recovered.

EXAMPLE 3

A photoprotective/sunscreen formulation in accordance with the invention was prepared in the form of a sunscreen cream containing:

| | | |
|---|---|---|
| (a) | Compound of Example 1 | 5 g |
| (b) | Mixture of cetylstearyl alcohol and cetylstearyl alcohol oxyethylenated with 33 mol of EO ("SINNOWAX AO" marketed by Henkel) | 7 g |
| (c) | Mixture of non-self-emulsifiable glyceryl mono- and distearate | 2 g |
| (d) | Cetyl alcohol | 1.5 g |
| (e) | $C_{12}-C_{15}$ alkyl benzoate ("FINSOLV TN" marketed by Witco) | 20 g |
| (f) | Polydimethylsiloxane | 1.5 g |
| (g) | Glycerol | 17.5 g |
| (h) | Fragrance, preservative qs | |
| (i) | Water qs | 100 g |

This cream was formulated according to the standard techniques for the preparation of emulsions, by dissolving the screening agent in the fatty phase containing the emulsifying agents, heating this fatty phase to about 70°–80° C. and adding, with vigorous stirring, the water which had been heated to the same temperature. Stirring was maintained for 10 to 15 minutes and, after permitting the composition to cool with moderate stirring, the fragrance and preservative were lastly added at about 40° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a photoprotecting effective amount of a polyorganosiloxane/polyorganosilane compound having one of the formulae (1) to (3):

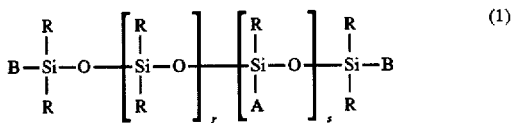

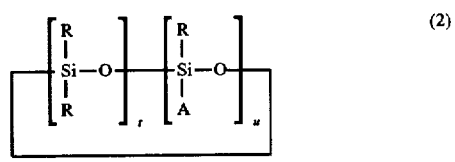

in which the radicals R, which may be identical or different, are each a $C_1-C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $CC_1-C_8$ alkyl radical or a phenyl radical; r is an integer ranging from 0 to 50, inclusive, and s is an integer ranging from 0 to 20, inclusive, with the proviso that, if s is zero, then at least one of the two radicals B is a radical A; u is an integer ranging from 1 to 6, inclusive, and t is an integer ranging from 0 to 10, inclusive, with the proviso that t+u is equal to or greater than 3; and the radical A is a monovalent radical bonded directly to a silicon atom and which has the following formula (4):

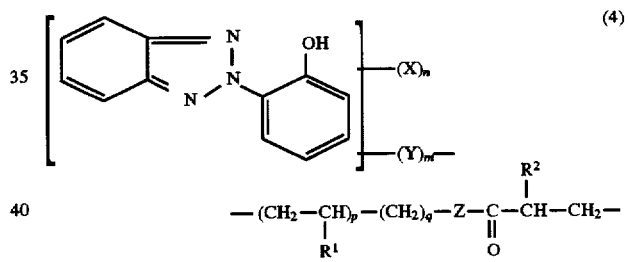

wherein n is an integer ranging from 0 to 3, inclusive, and the radicals X, which may be identical or different, are each a $C_1-C_8$ alkyl radical, a halogen atom or a $C_1-C_4$ alkoxy radical; m is 0 or 1, and Y is —O—, —COO—, —O(CH$_2$)$_v$—COO— or —(CH$_2$)$_w$—)CONH— in which v and w are integers ranging from 0 to 12, inclusive; p is 0 or 1; q is an integer ranging from 0 to 12, inclusive; Z is —O— or —NH—; $R^1$ is hydrogen or a $C_1-C_4$ alkyl radical; and $R^2$ is hydrogen or a methyl radical, a benzotriazole-substituted in a cosmetically acceptable vehicle, carrier or diluent therefor.

2. The sunscreen/cosmetic composition as defined by claim 1, said cosmetically acceptable vehicle, carrier or diluent comprising at least one fatty phase or at least one organic solvent.

3. The sunscreen/cosmetic composition as defined by claim 1, comprising an oil-in-water or water-in-oil emulsion.

4. The sunscreen/cosmetic composition as defined by claim 1, comprising from 0.1% to 20% by weight of said photoprotecting compound.

5. A method for protecting human skin and/or hair against the deleterious effects of ultraviolet irradiation, comprising topically applying thereto an effective amount of the sunscreen/cosmetic composition as defined by claim 1.

6. A method for protecting human skin and/or hair against the deleterious effects of solar radiation, comprising topically applying thereto an effective amount of the sunscreen/cosmetic composition as defined by claim 1.

7. The composition of claim 1, wherein the compound has formula (1).

8. The composition of claim 1, wherein the compound has formula (2).

9. The composition of claim 1, wherein the compound has formula (3).

10. The composition of claim 1, where in the compound of formulae (1) or (2), the radicals R are alkyl radicals.

11. The composition of claim 10, wherein said alkyl radicals are selected from the group consisting of methyl, ethyl, propyl, n-butyl, n-octyl and 2-ethylhexyl radicals.

12. The composition of claim 11, wherein said R radicals are methyl radicals.

13. The composition of claim 7, where in the compound of formula (1) the radicals B are alkyl radicals.

14. The composition as defined by claim 13, where in said compound of formula (1) radicals B are selected from the group consisting of methyl, ethyl, propyl, n-butyl, n-octyl and 2-ethylhexyl radicals.

15. The composition of claim 14, where in said compound of formula (1) said radicals B are methyl radicals.

16. The composition of claim 7, where in the compound of formula (1), r ranges from 0 to 3 and s ranges from 0 to 3.

17. The composition of claim 8, where in in the compound of formula (2), t+u ranges from 3 to 5.

18. The composition of claim 9, where in in the compound of formula (3), the radicals R' are selected from the group consisting of methyl, ethyl, propyl, n-butyl, n-octyl and 2-ethylhexyl radicals.

19. The composition of claim 18, said R' radicals being methyl radicals.

20. The composition as defined by claim 1, where in the formulae (1) to (3), n s other than zero and the radicals X are selected from the group consisting of methyl, tert-butyl and $C_1$–$C_4$ alkoxy radicals.

21. The composition of claim 20, wherein said radicals X are methyl or methoxy radicals.

22. The composition as defined by claim 21, wherein said radicals X are methoxy radicals.

23. The composition of claim 1, where in the compound of formulae (1) to (3), m is other than zero and Y is —O— or —NH—.

24. The composition as defined by claim 1, where in the compound of formulae (1) to (3), p is other than zero and $R^1$ is hydrogen.

25. The composition of claim 1, where in the compound of formulae (1) to (3), g ranges from 0 to 3.

26. The composition of claim 1, wherein in the formula (1) to (3), the radical —(Y)$_m$—(CH$_2$—CHR$^1$)p—(CH$_2$)q—Z—CO—CHR$^2$—CH$_2$— is bonded to the 3-, 4-, 4'-, or 5-position of the benzotriazole nucleus.

27. The composition of claim 26, said bonding being to the 3-, 4- or 5-position of the benzotriazole nucleus.

28. The composition as defined by claim 1, where in the compound of formulae (1) to (3), the radical(s) X is/are bonded to the 3-, 4-, 4'-, 5- and/or 6-positions of the benzotriazole nucleus.

29. The method of claim 5, wherein the composition comprises a compound having the formula (1).

30. The method of claim 5, wherein the composition comprises a compound having the formula (2).

31. The method of claim 28, wherein the composition comprises a compound having the formula (3).

32. The method of claim 29, wherein the composition comprises a compound having the formula (1).

33. The method of claim 29, wherein the composition comprises a compound having the formula (2).

34. The method of claim 29, wherein the composition comprises a compound having the formula (3).

* * * * *